United States Patent
El Meski et al.

(10) Patent No.: US 8,663,678 B2
(45) Date of Patent: Mar. 4, 2014

(54) SOLID DOSAGE FORM FOR THE OCULAR ADMINISTRATION OF AN ACTIVE PRINCIPLE, A SOLUBLE, SOLID OPHTHALMIC INSERT AND THE PRODUCTION METHOD THEREOF

(75) Inventors: Saïd El Meski, Dijon (FR); Philippe Tourrette, La Rochelle (FR); Jean-Marc Aiache, Clermont-Ferrand (FR); Marie Di Battista, Arveyres (FR); Gilbert Serpin, Clermont-Ferrand (FR)

(73) Assignee: Laboratoires Thea, Clermont-Ferrand (FR)

( * ) Notice: Subject to any disclaimer, the term of this patent is extended or adjusted under 35 U.S.C. 154(b) by 1226 days.

(21) Appl. No.: 10/499,058

(22) PCT Filed: Dec. 17, 2002

(86) PCT No.: PCT/FR02/04384
§ 371 (c)(1),
(2), (4) Date: Dec. 6, 2004

(87) PCT Pub. No.: WO03/051330
PCT Pub. Date: Jun. 26, 2003

(65) Prior Publication Data
US 2005/0118231 A1 Jun. 2, 2005

(30) Foreign Application Priority Data
Dec. 18, 2001 (FR) ...................................... 01 16377

(51) Int. Cl.
*A61K 31/716* (2006.01)
*A61F 2/00* (2006.01)

(52) U.S. Cl.
USPC ............................................ 424/427; 514/57

(58) Field of Classification Search
None
See application file for complete search history.

(56) References Cited

U.S. PATENT DOCUMENTS

| | | | | |
|---|---|---|---|---|
| 3,993,071 A | * | 11/1976 | Higuchi et al. | 424/428 |
| 4,179,497 A | | 12/1979 | Cohen et al. | |
| 4,343,787 A | | 8/1982 | Katz | |
| 4,518,433 A | * | 5/1985 | McGinley et al. | 106/170.38 |
| 5,543,156 A | * | 8/1996 | Roorda et al. | 424/484 |
| 2001/0047025 A1 | * | 11/2001 | Garcia et al. | 514/410 |

FOREIGN PATENT DOCUMENTS

| | | |
|---|---|---|
| EP | 0 316 838 | 5/1989 |
| EP | 0 561 695 | 9/1993 |
| WO | WO 94 05257 | 3/1994 |

OTHER PUBLICATIONS

Ethyl Cellulose_Chemical Properties at www.chemicalbook.com/ProductChemicalPropertiesCB6165620_EN.htm.*
Cellulose_Acetate_MSDS www.sciencelab.com/msds.php?msdsld=956.*
Disintegrate Definition at http://www.merriam-webster.com/dictionary/disintegrate (retrieved from the internet May 24, 2013).*

* cited by examiner

*Primary Examiner* — Dennis Heyer
(74) *Attorney, Agent, or Firm* — Young & Thompson

(57) ABSTRACT

A solid dosage form for the ocular administration of an active principle includes at least one biocompatible, water-soluble excipient for ophthalmic use. The form is obtained using a method which is selected from among the following: direct compression, dry compression, wet compression, compression of a lyophilizate, the compression being carried out a temperature below 45° C., or lyophilization, such that the form can disintegrate and release the active principle in the conjunctival sac. The invention also relates to an ophthalmic insert having the aforementioned dosage form which is appropriately dimensioned for ocular administration.

16 Claims, No Drawings

SOLID DOSAGE FORM FOR THE OCULAR ADMINISTRATION OF AN ACTIVE PRINCIPLE, A SOLUBLE, SOLID OPHTHALMIC INSERT AND THE PRODUCTION METHOD THEREOF

The present invention relates to a solid dosage form for the ocular administration of an active principle, to a solid and soluble ophthalmic insert obtained from this form and to a process for the manufacture of such an insert.

The dosage form of the invention can be used without distinction in human or veterinary medicine for a local or systemic action.

Numerous pharmaceutical compositions are used in the treatment of eye disorders. These compositions are generally liquid forms, gels or ointments. Because of the secretion and the drainage of the lacrimal fluid, these forms do not make possible a contact time sufficient for satisfactory penetration of the active principle or principles at the cornea.

Dry solid forms of the insert type to be deposited in the conjunctival cul-de-sac have appeared since 1973. These inserts are generally composed of a matrix of insoluble polymers intended to release the active principle in a prolonged fashion. They therefore have to be removed from the conjunctival cul-de-sac after a sufficient contact time. Such forms are particularly indicated when the prescribed treatment has to be longlasting or where it requires a prolonged contact time. The use of this type of insert is also desired for the administration of a precise dose of an active principle.

Such insoluble inserts can sometimes exhibit the disadvantage of releasing slowly the active principles retained in the matrix. They may also be incompatible when an immediate action is desired.

As a result of this insoluble matrix, the dose of active principle has to be increased and the release profile is not always controlled as a certain amount of active principle is not released by the polymer matrix. Another disadvantage of these forms is that they have to be removed after use with the risk of breakage of the insert during removal.

Biodegradable soluble ocular inserts have been developed from water-soluble biocompatible polymers. These inserts are also intended for a prolonged and controlled release of a medicinal substance by slow and gradual dissolution or swelling of the polymers used.

U.S. Pat. No. 4,179,497 discloses pilocarpine ophthalmic inserts based on a hydroxypropylcellulose (HPC) matrix which are prepared by extrusion or by compression molding under hot conditions. The inserts obtained, which benefit from thermoplastic properties of HPC, are soft and flexible after compression. When administered in the eye, they soften and then dissolve slowly. The heat forming can decompose sensitive active principles.

It would therefore be desirable to have available solid dosage forms for the ocular administration of active principles make possible rapid release of the latter.

It would also be desirable to have available solid dosage forms for the ocular administration of active principles which make possible controlled release and soluble ophthalmic inserts which make possible rapid and controlled release of active principles.

It is generally always desirable to limit as far as possible the total number of ingredients, for example for reasons of cost or of interaction between the various constituents.

For this reason, a subject matter of the present invention is a solid dosage form for the ocular administration of active principles of the invention, characterized in that it comprises at least one water-soluble excipient biocompatible with an ophthalmic use and in that it is obtained by a process chosen from compression and lyophilization, so that it can disintegrate in the conjunctival cul-de-sac, and in particular a solid dosage form for the ocular administration of an active principle, characterized in that it comprises at least one water-soluble excipient biocompatible with an ophthalmic use and in that it is obtained by a process chosen from:
  direct compression,
  dry compression,
  wet compression,
  compression of a lyophilisate,
the compression being carried out at a temperature of less than 45° C., and
  lyophilization,
so that it can disintegrate and release the active principle in the conjunctival cul-de-sac.

The dosage form according to the invention is dry and inflexible.

The term "active principle" is to be understood, within the meaning of the present invention, as referring not only to a compound having a pharmacological action but also to a compound not having a pharmacological action but, for example, a physical action, which can be used, by way of illustration, in dry eye syndrome, or mechanical action.

The term "water-soluble" is understood to mean that the excipient is directly soluble or partially soluble in water, without passing through a gel stage.

The water-soluble excipient biocompatible with an ophthalmic use is advantageously chosen from water-soluble polymers.

The water-soluble excipient biocompatible with an ophthalmic use is, for example, chosen from carbohydrates, gums, sodium salts, calcium salts, magnesium salts, maltodextrins, cellulose derivatives, chitosans, destructured starches, partially hydrolyzed starches, crosslinked starches, polyvinyl alcohols and acrylic acid polymers.

The cellulose derivatives are preferably chosen from hydroxyalkylcelluloses, for example hydroxypropylcellulose.

The water-soluble excipient biocompatible with an ophthalmic use can be present at a concentration which can reach 99.9% by weight, preferably of between approximately 40 and approximately 99.5%, in particular between 50% and 99%, particularly between 60% and 95%.

According to the invention, the dosage form can additionally comprise conventional excipients for ophthalmic forms chosen from soluble lubricants, disintegrating agents, flow agents, polymeric coating agents and binders.

The soluble lubricant is, for example, chosen from sucroesters, polyethylene glycol, leucine and sodium borate.

The disintegrating agent is, for example, chosen from cellulose derivatives, croscarmellose sodium, crospovidone and povidone.

The cellulose derivatives are, for example, sodium carboxymethylcellulose.

The polymeric coating agents are generally chosen from thermoplastic cellulose derivatives. The thermoplastic cellulose derivatives are, for example, ethylcellulose and cellulose acetate. They have to be soluble in tears.

The number of excipients which a dosage form according to the invention includes is advantageously less than 5, preferably less than 4, in particular less than 3; especially, there is only a single excipient.

Under preferred conditions for implementation of the invention, the above dosage forms are substantially devoid of plasticizing agents, such as polyethylene glycol, glycerol or a hydroxypropyl-sucrose.

Under other preferred conditions for implementation of the invention, the above dosage forms are substantially devoid of preservative.

The term "substantially devoid" is understood to mean that the amount by weight of compound in question is less than 1%, in particular less than 0.5%, of the total weight of the final form. Under very particularly preferred conditions, the product in question is completely absent from the above dosage form.

The dosage form of the invention can additionally comprise a pharmacologically active substance or a nonpharmacologically active substance but, for example, with a physical or mechanical action.

The pharmacologically active substance is, for example, chosen from anesthetics, such as tetracaine, lidocaine or bupivacaine, antiallergics, such as sodium cromoglycate, corticoid antiinflammatories, such as dexamethasone sulfate or other dexamethasone salts, nonsteroidal antiinflammatories, such as diclofenac, indomethacin or ibuprofen, antibiotics, such as gentamicin or tobramycin, antibacterials or antivirals, such as acyclovir or ganciclovir, mydriatics, such as phenylephrine, tropicamide or atropine, antiglaucomas, such as pilocarpine or timolol, or prostaglandins. Mention may also be made of antiseptics, such as ciclosporin, healing agents, diagnostic aids, tear substitutes, vasoconstrictors, miotics, antimycotics and antiphlogistics.

The pharmacologically active substance can be chosen in order to have a local action or in order to have a systemic action.

A pharmacologically inactive substance can, for example, be hydroxypropylcellulose, which makes it possible to treat dry eye syndrome.

A person skilled in the art will easily determine the amount of pharmacologically active substance according to the nature of the substance and the therapeutic effect desired.

The dosage form of the invention is advantageously sterile and packaged individually or as multidoses, preferably in a device which facilitates its administration.

The excipient or excipients and the implementation of the process, for example the compression force, will advantageously be chosen by a person skilled in the art in order to confer, on a dosage form according to the invention, a disintegration time of less than two hours, preferably of less than one hour, especially of less than 45 min, particularly of less than 30 min, very particularly of less than 15 min. The disintegration can, for example, occur within 2 min.

For example, by adding a disintegrating agent, a shortening of the disintegration time is obtained.

The solid dosage forms for ocular administration which are a subject matter of the present invention have very advantageous physicochemical properties. In particular, they make possible rapid release of the active principle or principles. They also make possible controlled release of these active principles.

These properties are illustrated below in the experimental part. They justify the use of the solid dosage forms for ocular administration which are described above as forms for transportation, in particular of drugs.

The solid dosage forms for ocular administration according to the present invention are used, for example, in the treatment, both curative and preventive, of eye inflammation, dry eye syndrome or eye allergy, as well as in anesthesia.

The dosage form of the invention can be used without distinction in human or veterinary medicine for a local or systemic action.

For this reason, another subject matter of the invention is an ophthalmic insert composed of a dosage form as described above and having dimensions appropriate for ocular administration.

The dosage form constituting the ophthalmic insert advantageously has a length of between approximately 1 mm and approximately 10 mm, for example of between approximately 2 mm and approximately 5 mm, for an oblong insert. An insert with a circular shape will, for example, have a diameter which can range up to approximately 10 mm, in particular of between approximately 1 and approximately 4 mm.

The dosage form of the invention can be prepared in particular:
  by direct compression,
  by dry compression,
  by wet compression,
  by compression of a lyophilisate. It is possible, for this purpose, to prepare a lyophilisate based on a mixture, in particular in equal parts, between an active principle and mannitol, to mix this lyophilisate, for example, with hydroxypropylcellulose and PEG 6000, preferably after homogenization, to mix the combined product with a direct compression excipient, such as mannitol, and to compress using an appropriate die,
  by preparing a lyophilisate.

In order to prepare a dosage form according to the invention, it is possible in particular to proceed as follows:
  (a) mixing the various constituents in the powder form and direct compression of the mixture, the optional active principle and the excipients being sieved through a sieve with a mesh generally of between 0.100 and 0.630 mm; before direct compression, it is possible to add, for example, a humectant, such as hyaluronic acid, or a lubricating agent or then to prepare mixtures based on lactose, sugars or sucrose, such as Microcristal 120® or Compressuc®, of different particle size.
  (b) granulation or coating of all or part of the excipients and compression;
  (c) dissolution of the active principle in a solvent, such as an aqueous or saline solution and preferably a solution based on a saccharide, such as mannitol or sorbitol, followed by the evaporation of the solvent according to the lyophilization technique.

The compression is carried out at a temperature of less than 45° C., preferably of less than 35° C., especially of less than 30° C., particularly of less than 25° C. and very particularly at ambient temperature.

In some cases, the process can be carried out under cold conditions (4° C., for example) to prevent possible decomposition of an active principle when it is thermally labile.

The preferred conditions for implementing the solid dosage forms for ocular administration which are described above also apply to the other subject matters of the invention which are aimed above.

Finally, a subject matter of the present application is the use of a solid dosage form comprising at least one water-soluble excipient biocompatible with an ophthalmic use which is obtained by the above processes, in order to disintegrate in the conjunctival cul-de-sac, for the ocular administration of an active principle.

The invention will now be illustrated described by the following examples.

EXAMPLE 1

A dosage form according to the invention is prepared in the form of an ophthalmic insert comprising tetracaine hydrochloride as pharmacologically active substance incorporated in the mixture of powders obtained from the following components of table I.

TABLE I

| Component | Percentage by weight |
|---|---|
| Tetracaine hydrochloride | 22 |
| Direct compression lactose | 78 |

The direct compression lactose used is the lactose sold by BASF under the name Ludipress® LCE.

The active principle and the excipient are sieved through a sieve with a mesh of 0.400 mm. They are subsequently weighed and mixed for 5 to 10 minutes.

An ophthalmic insert is subsequently obtained by carrying out a direct compression of the mixture obtained on a rotary tableting machine equipped with 12 dies of oblong shape having a length of 4.3 mm and a width of 2.3 mm.

The dissolution time of the ophthalmic insert obtained is 4 minutes.

EXAMPLE 2

A dosage form is prepared from the components of table II according to the procedure of example 1.

TABLE II

| Component | Percentage by weight |
|---|---|
| Tetracaine hydrochloride | 9 |
| Direct compression lactose | 86 |
| Crospovidone | 5 |

The direct compression lactose used is the lactose sold by BASF under the name Ludipress® LCE.

The crospovidone used as disintegrating agent is sold by BASF under the name Kollidon® CL-M.

An ophthalmic insert is obtained as in example 1.

The dissolution time of the ophthalmic insert obtained is 2.5 minutes.

EXAMPLE 3

A dosage form is prepared from the components of table III according to the procedure of example 1.

TABLE III

| Component | Percentage by weight |
|---|---|
| Tetracaine hydrochloride | 10 |
| Direct compression lactose | 78 |
| Crospovidone | 12 |

The direct compression lactose used is the lactose sold by BASF under the name Ludipress®.

An ophthalmic insert is obtained as in example 1 or 2.

The dissolution time of the ophthalmic insert obtained is 4.5 minutes.

EXAMPLE 4

A dosage form is prepared from the components of table IV according to the procedure of example 1.

TABLE IV

| Components | Percentage |
|---|---|
| Lidocaine hydrochloride | 3.3 |
| Polyethylene glycol 6000 | 10 |
| Direct compression lactose | 86.7 |

The direct compression lactose used is the lactose sold by BASF under the name Ludipress® LCE.

An ophthalmic insert is obtained as in example 1 or 2.

The dissolution time of the ophthalmic insert obtained is 2 minutes.

EXAMPLE 5

A dosage form is prepared from the components of table V according to the procedure of example 1.

TABLE V

| Component | Percentage |
|---|---|
| Tetracaine hydrochloride | 3.3 |
| Hydroxyethylcellulose | 5 |
| Polyethylene glycol 6000 | 10 |
| Direct compression lactose | 81.7 |

The direct compression lactose used is the lactose sold by BASF under the name Ludipress® LCE.

An ophthalmic insert is obtained as in example 1 or 2.

The dissolution time of the ophthalmic insert obtained is 3 minutes.

EXAMPLE 6

A dosage form is prepared from the components of table VI according to the procedure of example 1.

TABLE VI

| Components | Percentage |
|---|---|
| Tetracaine hydrochloride | 11.3 |
| Hydroxypropylmethylcellulose | 5 |
| Sucroesters | 2 |
| Direct compression lactose | 81.7 |

The direct compression lactose used is the lactose sold by BASF under the name Ludipress® LCE.

An ophthalmic insert is obtained as in example 1 or 2.

The dissolution time of the ophthalmic insert obtained is 4 minutes 50 seconds.

It is obvious to a person skilled in the art that the same active principle, an anesthetic, was used solely to make possible comparisons of the dissolution times but that any active principle which can be used in ophthalmology can be incorporated in the composition according to the invention.

EXAMPLE 7

Dosage form Prepared by Lyophilization/Compression

A dosage form according to the invention is prepared from the components of the following table:

| Components | Percentage by weight |
| --- | --- |
| Lyophilized mixture (lactoferrin + mannitol) | 46 |
| HPC (Klucel ® EP Pharm 100) | 31.2 |
| Direct compression mannitol (Pearlitol ® 100 SD) | 17 |
| PEG 6000 | 5.8 |

A lyophilisate is prepared based on a mixture, in equal parts, between the active principle (lactoferrin) and the mannitol,
the lyophilisate is homogenized,
the lyophilisate is mixed with the HPC and the PEG 6000,
the mixture is mixed with the direct compression mannitol,
compression is carried out to produce an insert according to the invention,
primary and then secondary packaging is carried out.

The ophthalmic insert obtained is a dosage form with a mean weight of 12 mg which is resistant to splitting (hardness of 40 N evaluated in a hardness test according to the European Pharmacopoeia).

The direct compression mannitol is added to improve the flow of the powder and to obtain better compression of the lyophilisate mixture obtained.

EXAMPLE 8

Dosage Formula Prepared By Compression After Wet Granulation

A dosage form is prepared from the components of the following table:

| Components | Percentage by weight |
| --- | --- |
| Diclofenac | 1.3 |
| HPMC (Metolose ® 90 SH), 1st portion | 20 |
| HPMC (Metolose ® 90 SH), 2nd portion | 1.3 |
| Direct compression lactose | 77.4 | the diclofenac and the first portion of the HPMC are mixed,
a wet granulation is carried out with a water/ethyl alcohol mixture,
the granulated product is dried at 42° C. for 2 hours and is sieved,
the sieved granules are mixed with the second portion of the HPMC,
the direct compression lactose is added and the 500 g of granules obtained are compressed to produce compounds with a mean weight of 12 mg which disintegrate over 1H 30.

By varying the percentages of the components, it is possible to vary the dissolution times of the insert obtained. This time can be approximately 20 min, sometimes between 1H and 30 and 2 hours, but it can vary and can reach 8 hours, indeed even a disintegration time of between 12 and 24 hours.

EXAMPLE 9

Dosage Formula Prepared by Compression After Wet Granulation

A dosage form is prepared from the components of the following table:

| Components | Percentage by weight |
| --- | --- |
| Diclofenac | 1.2 |
| Leucine (Fluka) | 20 |
| Leucine (Sigma) | 33.8 |
| Leucine (Sigma) (external phase) | 1.2 |
| Direct compression lactose | 38.8 | the diclofenac and the HPMC are mixed,
then the Fluka leucine and the Sigma leucine are added,
a wet granulation is carried out with a water/ethyl alcohol mixture on the mixture obtained,
the grain is dried at 42° C. for 2 hours and is sieved,
the grain obtained is mixed with the remaining leucine, positioned as an external phase,
the direct compression lactose is added,
the 500 g of granules obtained are compressed, the compression force being adjusted in order for the ophthalmic insert manufactured, with a mean weight of 12 mg, to make possible release of diclofenac over at least eight hours.

The invention claimed is:

1. A solid dosage form for the ocular administration of an active principle, consisting of:
a compressed powder mixture or compressed granulation, wherein said compressed powder mixture or compressed granulation comprises:
a pharmacologically active substance,
at least one of a disintegrating agent and a lubricating agent, said disintegrating agent being selected from the group consisting of sodium carboxymethylcellulose, croscarmellose sodium, crospovidone and povidone, and said lubricant being selected from the group consisting of sucroesters, polyethylene glycol, leucine and sodium borate, and
at least one water-soluble excipient biocompatible with an ophthalmic use selected from the group consisting of carbohydrates, gums, sodium salts, calcium salts, magnesium salts, maltodextrins, hydroxyalkylcelluloses, carboxymethylcelluloses, chitosans, destructured starches, partially hydrolyzed starches, crosslinked starches, polyvinyl alcohols and acrylic acid polymers, said at least one water-soluble excipient is directly soluble or partially soluble in water, without passing through a gel state,
wherein said compressed powder mixture or compressed granulation is obtained by a process selected from the group consisting of:
direct compression,
dry compression,
wet compression, and
compression of a lyophilisate, and
the compression is carried out at a temperature of less than 45° C. and at a sufficient compression force so that said compression process in combination with said at least one water-soluble excipient confer onto said dosage form a disintegration time of less than two hours to release the active principle in the conjunctival cul-de-sac.

2. The dosage form according to claim 1, wherein the water-soluble excipient biocompatible with an ophthalmic use is hydroxypropylcellulose.

3. The dosage form according to claim 1, wherein the water-soluble excipient is present at a concentration of between approximately 40 and approximately 99.5% by weight.

4. The dosage form according to claim 1, wherein said compressed powder mixture or compressed granulation additionally comprises at least one excipient selected from the group consisting of flow agents, polymeric coating agents and binders.

5. The dosage form according to claim 1, wherein the pharmacologically active substance has a local action.

6. The dosage form according to claim 1, wherein the pharmacologically active substance has a systemic action.

7. The dosage form according to claim 1, wherein said dosage form is sterile and packaged individually or as multidoses.

8. An ophthalmic insert consisting of the dosage form according to claim 1, wherein said dosage form has dimensions appropriate for ocular administration.

9. The ophthalmic insert according to claim 8, wherein the dosage form has a length of between approximately 1 mm and approximately 10 mm or a diameter which can range up to approximately 10 mm.

10. The ophthalmic insert according to claim 8, wherein the dosage form has a length of between approximately 2 mm and approximately 5 mm or a diameter of between approximately 1 and approximately 4 mm.

11. The dosage form according to claim 1, wherein the water-soluble polymer biocompatible with an ophthalmic use is a carbohydrate.

12. A solid dosage form for the ocular administration of an active principle, comprising:
a compressed powder mixture or granulation comprising:
an active principle; and
lactose, sugars or sucrose as water-soluble excipients biocompatible with an ophthalmic use, said lactose, sugars or sucrose being sole water-soluble excipients in said compressed powder mixture or granulation; and
a coating on said compressed powder mixture or granulation, said coating comprising at least one of ethylcellulose or cellulose acetate,
wherein
said powder mixture or granulation is sufficiently compressed,
and substantially devoid of plasticizing agents so that said solid dosage form disintegrates in less than two hours to release the active principle in the conjunctival cul-de-sac.

13. The dosage form according to claim 12, wherein said compressed powdered mixture or granulation comprises said lactose, sugars or sucrose in an amount of 38.8% to 86.7%.

14. A solid dosage form for the ocular administration of an active principle, consisting of:
an active principle; and
at least one biocompatible excipient selected from the group consisting of carbohydrates, gums, sodium salts, calcium salts, magnesium salts, maltodextrins, hydroxylalkylcelluloses, carboxymethylcelluloses, chitosans, destructured starches, partially hydrolyzed starches, crosslinked starches, polyvinyl alcohols, and acrylic acid polymers,
wherein said solid dosage form is a compressed powder mixture or a compressed granulation, and said solid dosage form disintegrates in less than two hours to release the active principle in the conjunctival cul-de-sac.

15. The dosage form according to claim 11, wherein said carbohydrate is lactose, sugars or sucrose in an amount of 38.8% to 86.7% of said compressed powder mixture or compressed granulation.

16. The dosage form according to claim 12, wherein said compressed powdered mixture or granulation further comprises at least one of a disintegrating agent and a lubricating agent, said disintegrating agent being selected from the group consisting of croscarmellose sodium, crospovidone and povidone, and said lubricant being selected from the group consisting of sucroesters and leucine.

* * * * *

UNITED STATES PATENT AND TRADEMARK OFFICE
CERTIFICATE OF CORRECTION

PATENT NO.       : 8,663,678 B2                    Page 1 of 1
APPLICATION NO.  : 10/499058
DATED            : March 4, 2014
INVENTOR(S)      : El Meski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1315 days.

Signed and Sealed this
Twenty-ninth Day of September, 2015

Michelle K. Lee
*Director of the United States Patent and Trademark Office*